(12) United States Patent
Qiao et al.

(10) Patent No.: US 8,163,559 B2
(45) Date of Patent: Apr. 24, 2012

(54) WHITE BLOOD CELL DIFFERENTIATION REAGENT AND METHOD

(75) Inventors: Yanmei Qiao, Nanshan (CN); Bing Liu, Nanshan (CN); Xiangping Meng, Nanshan (CN); Wenjuan Xu, Nanshan (CN); Mulong Liu, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 13/016,571

(22) Filed: Jan. 28, 2011

(65) Prior Publication Data

US 2011/0151562 A1 Jun. 23, 2011

Related U.S. Application Data

(62) Division of application No. 12/337,381, filed on Dec. 17, 2008, now abandoned.

(30) Foreign Application Priority Data

Dec. 18, 2007 (CN) .................. 2007 1 01252090

(51) Int. Cl.
*G01N 33/48* (2006.01)
*C12N 5/078* (2010.01)

(52) U.S. Cl. .............. 436/10; 436/8; 436/17; 436/18; 436/63; 436/164; 436/166; 436/174; 435/2

(58) Field of Classification Search ............... 436/8, 10, 436/17, 18, 63, 164, 166, 174, 175; 422/73, 422/82.05, 82.09; 435/2
See application file for complete search history.

(56) References Cited

U.S. PATENT DOCUMENTS

| | | | |
|---|---|---|---|
| 4,751,179 A | 6/1988 | Ledis et al. | |
| 5,155,044 A | 10/1992 | Ledis et al. | |
| 5,264,369 A | 11/1993 | Sakata et al. | |
| 5,516,695 A | 5/1996 | Kim et al. | |
| 5,618,733 A | 4/1997 | Sakata et al. | |
| 5,677,183 A | 10/1997 | Takarada et al. | |
| 5,747,343 A | 5/1998 | Tsuchiya et al. | |
| 5,958,776 A | 9/1999 | Sakata et al. | |
| 6,664,110 B1 | 12/2003 | Tsuji et al. | |
| 7,413,905 B2 | 8/2008 | Xu et al. | |
| 7,416,891 B2 | 8/2008 | Xu et al. | |
| 7,449,337 B2* | 11/2008 | Deka et al. | 436/17 |
| 2007/0269896 A1 | 11/2007 | Xu et al. | |
| 2007/0275469 A1 | 11/2007 | Xu et al. | |

FOREIGN PATENT DOCUMENTS

CN 1126836 A 7/1996

OTHER PUBLICATIONS

Steadman's Medical Dictionary, 28th Edition, 1-2 (2005), accessed on Oct. 25, 2010.
Reezal et al., "Effect of Low-Osmolality Nutrient Media on Growth and Culturability of Campylobacter Species", App. Env. Micro. 64 (12): 4643-4649 (1998).
Gold et al., "Enzymatic Methylation of Ribonucleic Acid and Deoxyribonucleic Acid", J. Biol. Chem. 239 (11): 3866-3874 (1964).
Ohbu et al., "Binding Characteristics of Ionic Surfactants With Human Hair", Colloid & Polymer Science 264: 798-802 (1986).
Aldrich Catalog, entry 31, 870-1, Bromocresol Green, p. 247, 200-2001.
Yamamoto et al., "Liquid-Liquid Distribution of Ion-Associated of Acidic Dyes With Quaternary Ammonium Counter-Ions", Talanta 38 (5): 477-482 (1991), abstract only.
Office Action dated Nov. 4, 2010 for U.S. Appl. No. 12/337,381.
Response to Election Restriction dated Sep. 16, 2010 for U.S. Appl. No. 12/337,381.
Response to Election Restriction dated Jun. 8, 2010 for U.S. Appl. No. 12/337,381.
Requirement for Election Restriction dated May 13, 2010 for U.S. Appl. No. 12/337,381.

* cited by examiner

*Primary Examiner* — Maureen Wallenhorst
(74) *Attorney, Agent, or Firm* — Kory D. Christensen; Stoel Rives LLP

(57) ABSTRACT

A reagent for four-part differentiation of white blood cells is provided. In one embodiment the reagent has an osmolality below 50 mOsm/kg $H_2O$. A method for differentiating white blood cells using the reagent is also provided. The disclosure provides for a rapid lysis of red blood cells and four-part differentiation of white blood cells. The reagent may be simple in components and a surfactant is not necessary, but optional. A wide range of pH values may be suitable for the reagent.

12 Claims, 3 Drawing Sheets

WHITE BLOOD CELL DIFFERENTIATION
REAGENT AND METHOD

RELATED APPLICATIONS

This application is a divisional of U.S. patent application Ser. No. 12/337,381, filed Dec. 17, 2008, now abandoned, titled "WHITE BLOOD CELL DIFFERENTIATION REAGENT AND METHOD," which claims priority to Chinese Patent Application No. 200710125209.0, filed Dec. 18, 2007, for "WHITE BLOOD CELL DIFFERENTIATION REAGENT AND METHOD," the disclosures of which are fully incorporated herein by reference.

TECHNICAL FIELD

The present disclosure relates to a cell differentiation reagent and a method for differentiating cells, and in particular, to a reagent for a four-part differentiation of white blood cells in the blood and a method for the differentiation detection of white blood cells in the blood using the reagent.

BRIEF SUMMARY

Reagents for four-part differentiation of white blood cells in blood are disclosed. Methods for differentiation detection of white blood cells in blood are also disclosed.

DETAILED DESCRIPTION

Figure 1:
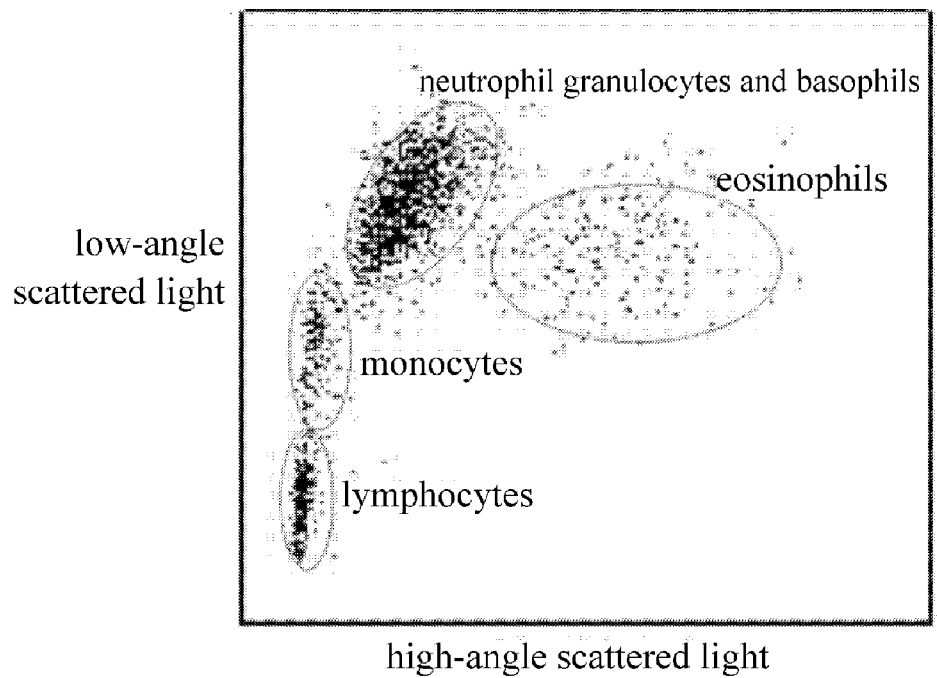
FIG. 1 shows the results of differentiation detection of white blood cells using one embodiment of a reagent for the differentiation of white blood cells.

In the field of clinical detection, differentiation detection and counting of cells in human whole blood samples are of great significance in clinical detection and diagnosis. In one embodiment, a reagent system is provided that can rapidly lyse red blood cells, has a relatively wide useful range for the pH value, is simple in components and can achieve four-part differentiation of white blood cells in one channel.

In one embodiment, a method for the differentiation detection of white blood cells in whole blood using the above-described reagent system is provided.

The present disclosure provides a reagent for differentiation of white blood cells into four groups, i.e., three groups corresponding to lymphocytes, monocytes, and eosinophil granulocytes and one group corresponding to neutrophil and basophil granulocytes. In one embodiment, the reagent has an osmolality below 50 mOsm/kg $H_2O$.

Further, in one embodiment the reagent has a pH in a range of between 4-12.

In a particular embodiment, the reagent for differentiation of white blood cells consists of water as the solvent and, optionally, at least one substance selected from the following: i) an inorganic salt, ii) a surfactant, iii) an organic compound having a hydrophobic group and an anionic group, and iv) a buffer.

In one embodiment, the inorganic salt is selected from at least one of the following: NaCl, KCl, LiCl, $Na_2SO_4$, $K_2SO_4$, and the like.

The surfactant is able to lyse red blood cells and partly damage membranes of white blood cells, and the surfactant may be a cationic surfactant, an anionic surfactant or a zwitterionic surfactant.

The organic compound may bind with cations in white blood cells to engender a morphological difference among various white blood cells. The hydrophobic group of the organic compound may be selected from aromatic groups, hydrocarbonyl groups having more than six carbon atoms or heterocyclyl groups having more than six carbon atoms. The anionic group of the organic compound may be a carboxylate group or a sulfonate group.

In a particular embodiment, the organic compound may be an acidic pigment. Alternatively, the organic compound is terephthalic acid, phthalic acid, chromotropic acid, naphthalenesulfonic acid, or a derivative or a salt thereof.

The present disclosure further provides a method for differentiating white blood cells in whole blood. The method comprises mixing the reagent described herein for differentiation of white blood cells with a whole blood sample, and then detecting information regarding the size and morphology of the cells.

Specifically, one exemplary method comprises mixing the reagent described herein for differentiation of white blood cells with a whole blood sample in a ratio of 50:1 to 200:1 under a temperature from ambient temperature to 40° C. for 10-20 seconds, and then detecting the information regarding the size and morphology of the cells through low-angle scattered light and high-angle scattered light, respectively. The detection angle for the low-angle scattered light may be 2-5 degrees and the detection angle for the high-angle scattered light may be 8-20 degrees. The detection of scattered light can be accomplished using a photodiode sensor.

By way of example, one embodiment of the present disclosure achieves rapid lysis of red blood cells and four-part differentiation of white blood cells by virtue of the physical property of low osmolality of the reagent. The reagent system is simple in components. A reagent that has an osmolality below 50 mOsm/kg $H_2O$ and a pH value in the range of 4-12 may be used to achieve the four-part differentiation of white blood cells, wherein a surfactant is optional, but not essential, and therefore can be absent or used in a small amount. Potentially useful surfactants are not limited in variety and can be selected from a relatively wide range. The optional surfactant can be a cationic surfactant, an anionic surfactant, a zwitterionic surfactant or any combinations thereof. A wide range of pH values is also suitable for the reagent system, and in one embodiment, an accurate four-part differentiation of white blood cells can be achieved within the pH range of 4-12. The reagent system can maintain, to a large extent, the natural physiological state and/or immunochemical state of various subpopulations of white blood cells, and allow for four-part differentiation of white blood cells through a simple two-angle light scattering method. The differentiation detection of white blood cells using one embodiment of the reagent can be carried out not only at an ambient temperature, but also at higher temperatures, such as from ambient temperature to 40° C. Reaction at a high temperature may obviate the influence of ambient temperature on the reaction, thereby increasing reliability and stability of the results.

In one aspect, the reagent and method for the differentiation of white blood cells makes use of the physical property of hypotonicity of the reagent to achieve the purpose of lysing red blood cells and differentiating white blood cells. One exemplary reagent has an osmolality below 50 mOsm/kg $H_2O$ and a pH value in the range of 4-12. The osmolality of the exemplary reagent is not necessarily confined by a lower limit. By adding an exemplary reagent into a whole blood sample and detecting the information regarding the size and morphology of the white blood cells, these cells can be differentiated into four populations: lymphocytes, monocytes, eosinophil granulocytes and basophil granulocytes plus neutrophils.

There are a variety of substances that may be used for adjusting the osmolality of the solution. Those commonly-used substances for adjusting the osmolality below 50 mOsm/kg $H_2O$ include salts such as NaCl, KCl, LiCl, $Na_2SO_4$ and $K_2SO_4$ being most generally used. A buffering component, a surfactant, an organic compound having an anionic group, or the like that can be added into the system may also contribute to the osmolality of the reagent.

The reagent system can be optionally added with a surfactant. The present disclosure does not limit the variety of the optional surfactant and it can be a cationic surfactant, an anionic surfactant or a zwitterionic surfactant, or any combinations thereof. The optional surfactant can lyse red blood cells and partly damage the membranes of white blood cells.

The above-described ionic surfactant may be optionally added into the hypotonic reagent system disclosed to assist in hemolysis in an amount sufficient to help to lyse red blood cells and partly damage the membranes of white blood cells. The amount is usually 50-2000 mg/L, such as 200-1500 mg/L, or alternatively 500-1000 mg/L. But the amount can be suitably adjusted depending on the variety of the surfactant in use. The hemolytic effect of a surfactant is typically in direct proportion to its carbon chain length.

Typically the greater the number of carbon atoms, the stronger the hemolytic effect, and accordingly the smaller the amount to be used. However, regardless what variety of the surfactant or combination of surfactants is selected, the amount may be far less than that which results in the complete nakedness of the nucleus of the cells.

The reagent system disclosed may optionally include one or more organic compounds having anionic groups which can bind with the cations in white blood cells to engender morphological differences among white blood cells. Such compounds may include hydrophobic groups (such as aromatic groups, hydrocarbonyl groups having more than six carbon atoms and heterocyclyl groups having more than six carbon atoms, etc.) and anionic groups (such as carboxylate groups or sulfonate groups). They will become negatively charged in water and bind with white blood cells to change the morphology of the cells. Various acidic pigments may be useful, such as Acid Blue series, Direct Blue, Acid Green, Bromocresol Green, Acid Yellow, Acid Orange, Methyl Red, Methyl Orange, Aniline Blue, Alizarin Yellow, etc. Compounds other than pigments are terephthalic acid, phthalic acid, chromotropic acid, naphthalenesulfonic acid, as well as derivatives and salts thereof. Addition of such compounds, in amounts from 50 to 3000 mg/L, such as from 500 to 2000 mg/L, may help to differentiate eosinophils from other granulocytes in terms of size and morphology, but is not essential.

The reagent system disclosed may also contain buffers for adjusting pH. There are no particular requirements for the buffers, which can be commonly used buffering systems such as formic acid, acetic acid, boric acid, citric acid, succinic acid, MES, TRIS, HEPES, carbonic acid and the like. Different pH values of the reagent in the range of 4-12 show no absolute effect on the four-part differentiation of white blood cells. The buffers are typically used in an amount ranging from 10 to 100 mM.

In one embodiment, the physical property of hypotonicity of the reagent achieves the purpose of lysing red blood cells and differentiating white blood cells. Those reagents that have an osmolality below 50 mOsm/kg $H_2O$ and a pH value in the range of 4-12 are applicable to this embodiment. The above-mentioned four kinds of substances, i.e., inorganic salts, surfactants, organic compounds having hydrophobic groups and anionic groups as well as buffers, can all contribute to the osmolality of the reagent. In one embodiment where the osmolality is below 50 mOsm/kg $H_2O$ and a pH in the range of 4-12 are achieved, the reagent may, in addition to water as the solvent, only contain any one kind of the above-mentioned four kinds of substances, or contain more than one kind. For example, a reagent system that only contains a buffer can still achieve the functions disclosed with an osmolality below 50 mOsm/kg $H_2O$ and a pH value in the range of 4-12. Likewise, the aqueous solutions of such commonly used inorganic salts as NaCl, KCl, LiCl, $Na_2SO_4$ and $K_2SO_4$, etc., can be used for the four-part differentiation of white blood cells and achieve the desired effects, when according to one exemplary embodiment, they meet the osmolality and pH values described.

By mixing the above-described reagent with a whole blood sample in a ratio of 50:1 to 200:1 for 10-20 seconds, and then detecting the information regarding the size and morphology of the white blood cells, these cells can be differentiated into four groups, i.e., three groups corresponding to lymphocytes, monocytes, eosinophil granulocytes and one group corresponding to neutrophil and basophil granulocytes, and can be counted differentially. The detection of the size and morphology of the cells is accomplished through low-angle scattered light and high-angle scattered light, respectively. Low-angle scattered light reflects the information regarding the size of the cells and may be detected at an angle between 2-5 degrees. High-angle scattered light reflects the information regarding the morphology of the cells and may be detected at an angle between 8-20 degrees. The detection of scattered light can be accomplished using a photodiode sensor. Therefore, using the reagents disclosed, the four-part differentiation of white blood cells can be achieved with the simplest optical combination.

The reaction temperature for mixing the exemplary reagents with a whole blood sample can be at ambient temperature (25° C.) or a higher temperature (40° C.), or a fixed temperature between ambient temperature and 40° C. In one embodiment, the reaction is conducted at 37° C. A heating device may be sufficient to achieve a constant temperature above room temperature without the need of a refrigerating device, which reduces the cost in equipment. Moreover, a constant temperature may obviate the influence of ambient temperature on the reaction, thereby increasing reliability and stability of the results.

The present disclosure is further described in more detail by way of the specific examples as follows.

EXAMPLE 1

A reagent for four-part differentiation of white blood cells included the following components:

| | |
|---|---|
| Sodium chloride | 1 g |
| Adding water to | 1 L |
| pH | 5.3 |
| Osmolality | 34 mOsm/kg H$_2$O | wherein sodium chloride was used to adjust the osmolality. 10 μl of a whole blood sample was added into 0.8 ml of the above reagent, and the mixture was reacted at 37° C. for 10 seconds. Then the white blood cells were subjected to differentiation detection through low-angle and high-angle scattered light, with the detection angle being 2-5 degrees for low-angle scattered light and 8-20 degrees for high-angle scattered light. The results are shown in FIG. 1.

EXAMPLE 2

Figure 2:
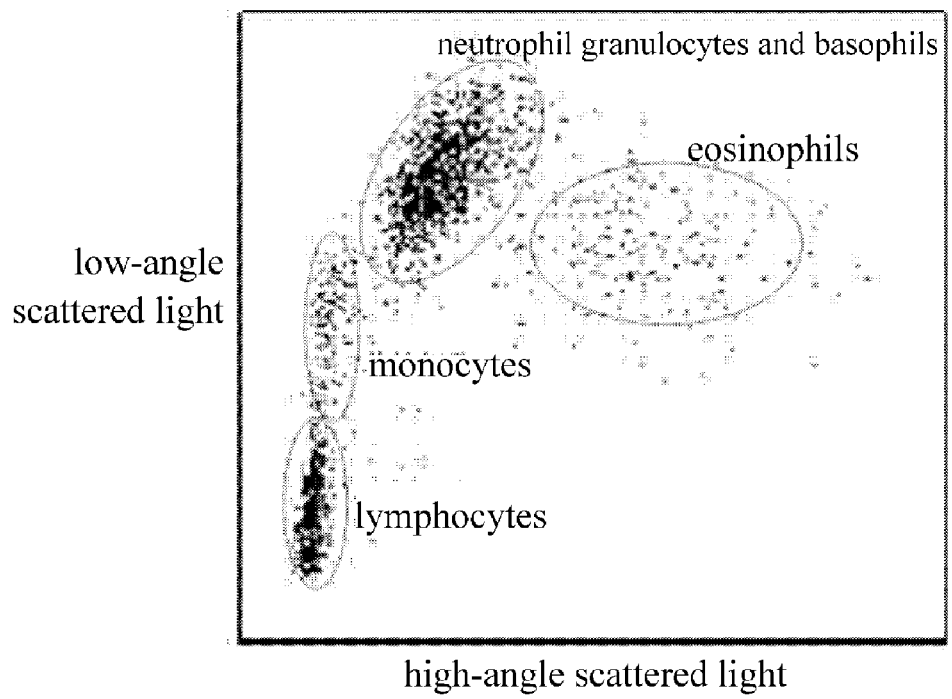
FIG. 2 shows the results of differentiation detection of white blood cells using another reagent for the differentiation of white blood cells.

A reagent for four-part differentiation of white blood cells included the following components:

| | |
|---|---|
| HEPES | 2.38 g |
| Bromocresol Green | 0.5 g |
| Adding water to | 1 L |
| pH | 7.0 |
| Osmolality | 15 mOsm/kg H$_2$O | wherein HEPES acted as a buffer, and Bromocresol Green was an organic compound having an anionic group. 10 μl of a whole blood sample were added into 1 ml of the above reagent, and the mixture was reacted at 37° C. for 10 seconds. Then the white blood cells were subjected to differentiation detection through low-angle and high-angle scattered light, with the detection angle being 2-5 degrees for low-angle scattered light and 8-20 degrees for high-angle scattered light. The results are shown in FIG. 2.

EXAMPLE 3

Figure 3:
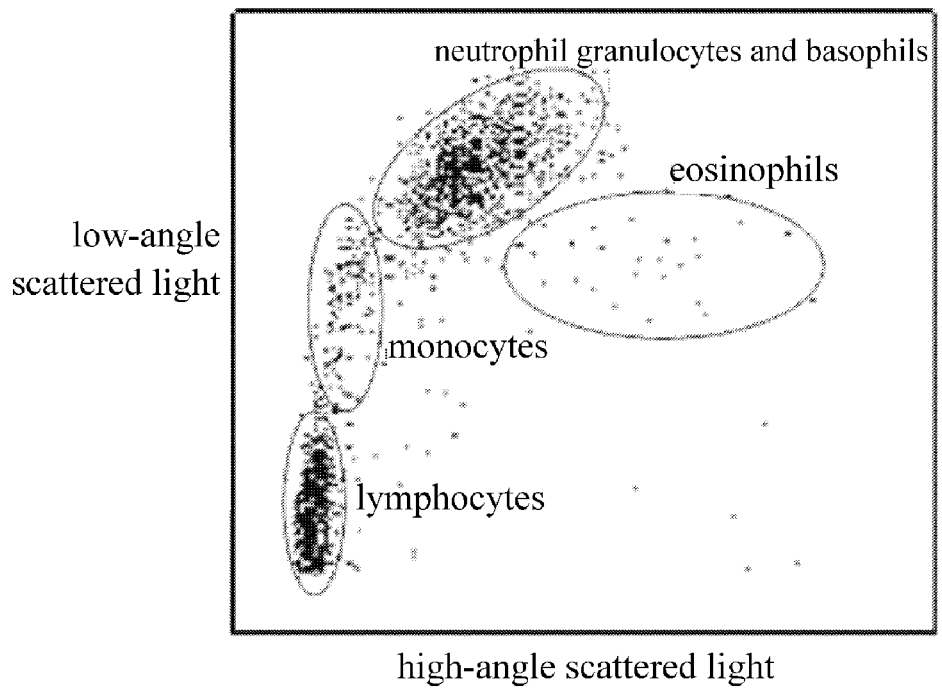
FIG. 3 shows the results of differentiation detection of white blood cells using a further reagent for the differentiation of white blood cells.

A reagent for four-part differentiation of white blood cells included the following components:

| | |
|---|---|
| Sodium carbonate | 2.38 g |
| Decyltrimethylammonium chloride | 0.5 g |
| Adding water to | 1 L |
| pH | 9.0 |
| Osmolality | 30 mOsm/kg H$_2$O | wherein sodium carbonate acted as a buffer, and decyltrimethylammonium chloride acted as a surfactant. 10 μl of a whole blood sample were added into 1.5 ml of the above reagent, and the mixture was reacted at 37° C. for 10 seconds. Then the white blood cells were subjected to differentiation detection through low-angle and high-angle scattered light, with the detection angle being 2-5 degrees for low-angle scattered light and 8-20 degrees for high-angle scattered light. The results are shown in FIG. 3.

EXAMPLE 4

Figure 4:
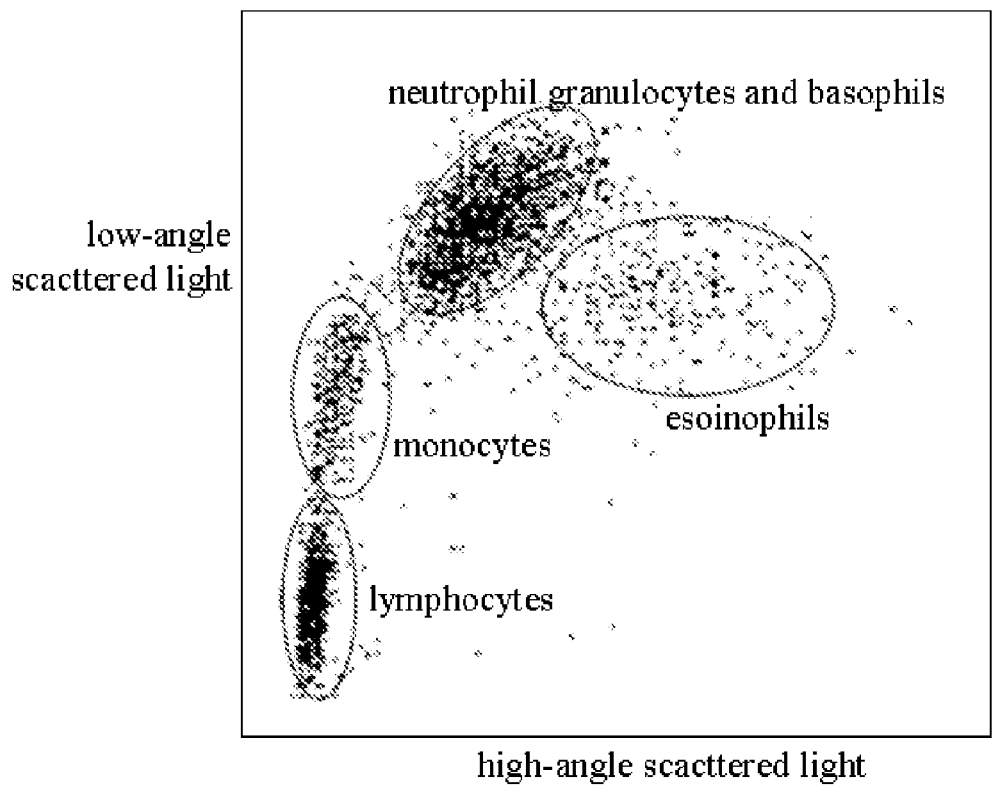
FIG. 4 shows the results of differentiation detection of white blood cells using a further reagent for the differentiation of white blood cells.

A reagent for four-part differentiation of white blood cells included the following components:

| | |
|---|---|
| Sodium acetate | 0.827 g |
| Acetic acid | 1 ml |
| Adding water to | 1 L |
| pH | 4.0 |
| Osmolality | 45 mOsm/kg H$_2$O | wherein sodium acetate acted as a buffer, and the same time it was used to adjust the osmolality. 10 μl of a whole blood sample was added into 1 ml of the above reagent, and the mixture was reacted at 37° C. for 10 seconds. Then the white blood cells were subjected to differentiation detection through low-angle and high-angle scattered light, with the detection angle being 2-5 degrees for low-angle scattered light and 8-20 degrees for high-angle scattered light. The results are shown in FIG. 4.

EXAMPLE 5

Figure 5:
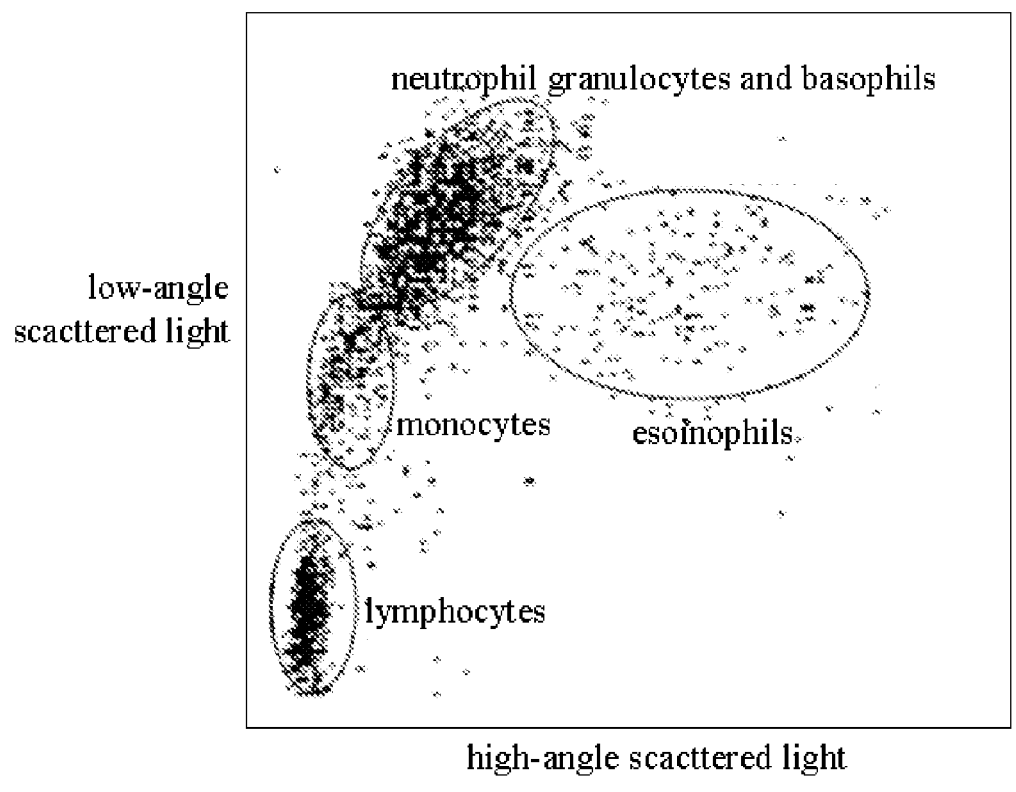
FIG. 5 shows the results of differentiation detection of white blood cells using a further reagent for the differentiation of white blood cells.

A reagent for four-part differentiation of white blood cells included the following components:

| | |
|---|---|
| Potassium chloride | 0.39 g |
| Adding water to | 1 L |
| pH | 6.9 |
| Osmolality | 5 mOsm/kg H$_2$O | wherein potassium chloride was used to adjust the osmolality. 10 μl of a whole blood sample was added into 1 ml of the above reagent, and the mixture was reacted at 37° C. for 10 seconds. Then the white blood cells were subjected to differentiation detection through low-angle and high-angle scattered light, with the detection angle being 2-5 degrees for low-angle scattered light and 8-20 degrees for high-angle scattered light. The results are shown in FIG. 5.

EXAMPLE 6

Figure 6:
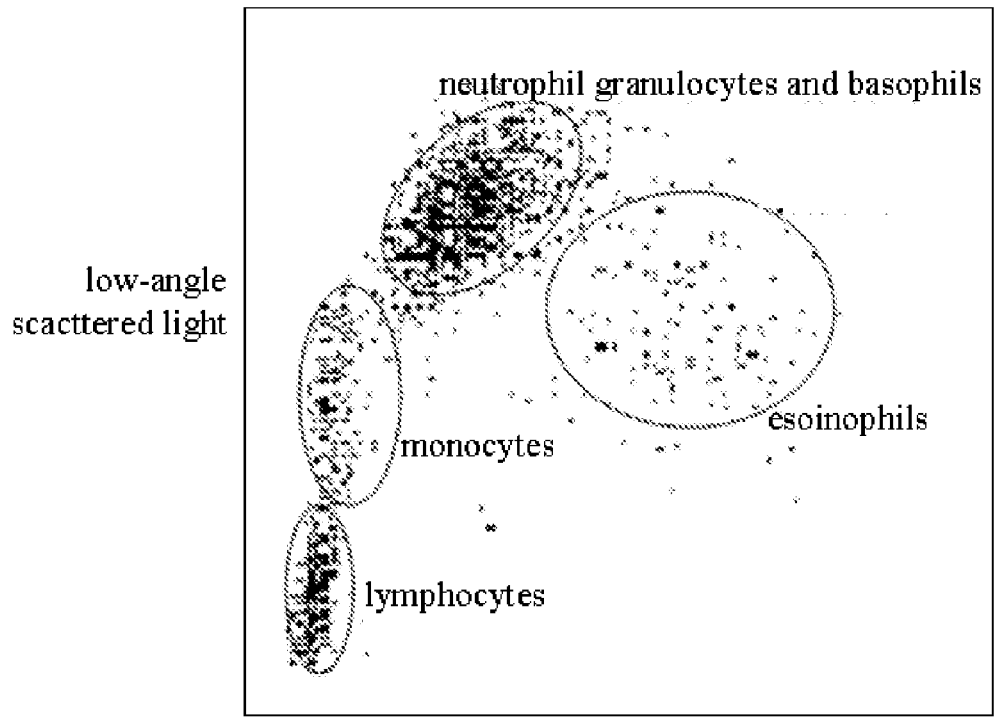
FIG. 6 shows the results of differentiation detection of white blood cells using a further reagent for the differentiation of white blood cells.

A reagent for four-part differentiation of white blood cells included the following components:

| | |
|---|---|
| Tris Base | 0.39 g |
| Adding water to | 1 L |
| pH | 11.6 |
| Osmolality | 20 mOsm/kg H$_2$O | wherein Tris Base acted as a buffer. 10 μl of a whole blood sample was added into 1.2 ml of the above reagent, and the mixture was reacted at 37° C. for 10 seconds. Then the white blood cells were subjected to differentiation detection through low-angle and high-angle scattered light, with the detection angle being 2-5 degrees for low-angle scattered light and 8-20 degrees for high-angle scattered light. The results are shown in FIG. 6.

EXAMPLE 7

The osmolality of a conventional reagent system was determined using surfactants structurally similar to a reagent disclosed in U.S. Pat. No. 5,677,183. The conventional reagent system included:
Decyltrimethylammonium bromide at a concentration of 1.5 g/L;

8-Anilino-1-naphthalenesulfonic acid, magnesium salt at a concentration of 2.0 g/L;
Brij-58 at a concentration of 3.0 g/L;
Phthalic acid at a concentration of 50 mM;
2-Phenoxy ethanol at a concentration of 2.5 mL/L;
Sodium Chloride at a concentration of 30 mM; and
Sodium hydroxide adjusting the reagent pH to 5.5;
wherein the osmolality was measured twice, with the average being 217 mOsm/kg $H_2O$. The osmolality of this conventional system is far in excess of the osmolality of the reagents provided in accordance with the present disclosure.

The above illustrations are for the purpose of describing the present disclosure in more detail in conjunction with particular examples. It is not intended that the present invention, as claimed, be limited to these particular embodiments. Simple deductions or replacements can be made by those skilled in the art without departing from the present disclosure, which shall be deemed to fall within the scope of the present invention, as claimed.

What is claimed is:

1. A method for differentiation of white blood cells, wherein the method comprises:
   obtaining a reagent for differentiation of white blood cells, the reagent comprising a composition configured for four-part differentiation of white blood cells, wherein the composition is free from a surfactant and has an osmolality below about 50 mOsm/kg $H_2O$;
   mixing the reagent with a whole blood sample in a ratio of 50:1 to 200:1 of reagent:whole blood sample under a temperature between ambient temperature and 40° C. for between 10-20 seconds;
   detecting information regarding the size and morphology of the white blood cells from the whole blood sample after mixing with the reagent through low-angle scattered light and high-angle scattered light respectively, wherein a detection angle for the low-angle scattered light is between 2-5 degrees and a detection angle for the high-angle scattered light is between 8-20 degrees; and
   differentiating the white blood cells into four groups, including three groups corresponding to lymphocytes, monocytes, and eosinophil granulocytes and one group corresponding to neutrophil and basophil granulocytes.

2. The method of claim 1, wherein obtaining the reagent comprises obtaining a reagent comprising a composition with pH value between 4-12.

3. The method of claim 2, wherein obtaining a reagent comprises obtaining a reagent comprising a composition with water as a solvent and at least one substance selected from at least one of the following: an inorganic salt and a buffer.

4. The method of claim 3, wherein the composition comprises an inorganic salt and the inorganic salt is selected from at least one of the following: NaCl, KCl, LiCl, $Na_2SO_4$ and $K_2SO_4$.

5. The method of claim 3, wherein the composition comprises a buffer and the buffer is selected from at least one of the following: HEPES, sodium carbonate and sodium acetate.

6. The method of claim 2, wherein obtaining the reagent comprises obtaining a reagent comprising a composition with water as a solvent and at least one substance selected from at least one of the following: an inorganic salt, an organic compound having a hydrophobic group and an anionic group, and a buffer.

7. The method of claim 6, wherein the composition comprises an inorganic salt and the inorganic salt is selected from at least one of the following: NaCl, KCl, LiCl, $Na_2SO_4$ and $K_2SO_4$.

8. The method of claim 6, wherein the composition comprises a buffer and the buffer is selected from at least one of the following: HEPES, sodium carbonate and sodium acetate.

9. The method of claim 6, wherein the composition comprises an organic compound and the organic compound is configured to bind with cations in white blood cells to engender a morphological difference among white blood cells; and
   wherein a hydrophobic group of the organic compound is selected from at least one of the following: an aromatic group, a hydrocarbonyl group having more than six carbon atoms and a heterocyclyl group having more than six carbon atoms.

10. The method of claim 6, wherein the composition comprises an organic compound and the organic compound is selected from at least one of the following: an acidic pigment, terephthalic acid, phthalic acid, chromotropic acid, naphthalenesulfonic acid, and a derivative or a salt of an acidic pigment, terephthalic acid, phthalic acid, chromotropic acid and naphthalenesulfonic acid.

11. The method of claim 1, wherein the composition has an osmolality below about 50 and above about 5mOsm/kg $H_2O$.

12. The method of claim 1, wherein the composition has an osmolality below about 45 and above about 5 mOsm/kg $H_2O$.

* * * * *